United States Patent [19]

Uehara et al.

[11] Patent Number: 5,446,181

[45] Date of Patent: Aug. 29, 1995

[54] METHOD AND APPARATUS FOR PREPARING 3-[N-(2-AMINOETHYL)]AMINO-PROPYLALKOXYSILANE

[75] Inventors: Katsuhiro Uehara; Mikio Endo; Hitoyuki Araki; Takeo Arai; Yasuhiro Kawase, all of Jouetsu, Japan

[73] Assignee: Shin-Etsu Chemical Co., Ltd., Tokyo, Japan

[21] Appl. No.: 140,955

[22] Filed: Oct. 25, 1993

[30] Foreign Application Priority Data

Oct. 26, 1992 [JP] Japan .................................. 4-310894

[51] Int. Cl.⁶ .............................................. C07F 7/10
[52] U.S. Cl. ...................................... 556/424; 422/212
[58] Field of Search ......................... 556/424; 422/212

[56] References Cited

U.S. PATENT DOCUMENTS

| 2,971,864 | 2/1961 | Speier | 556/424 X |
| 3,317,577 | 5/1967 | Ryan | 556/424 |
| 4,127,872 | 11/1978 | Lo | 556/424 |

FOREIGN PATENT DOCUMENTS 368279 11/1989 European Pat. Off. .

OTHER PUBLICATIONS

Chemical Abstracts, vol. 119, No. 23, 250165r, Dec. 6, 1993.

*Primary Examiner*—Paul F. Shaver
*Attorney, Agent, or Firm*—Millen, White, Zelano, & Branigan

[57] ABSTRACT

The invention produces a 3-[N-(2-aminoethyl)]aminopropylalkoxysilane in high yields by reacting a 3-chloropropylalkoxysilane with ethylene diamine. A distillation pot is charged with ethylene diamine and heated above the boiling point of ethylene diamine for evaporating ethylene diamine, which is then condensed into a liquid. The liquid ethylene diamine is mixed for reaction with a 3-chloropropylalkoxysilane in such a proportion to give a molar ratio of ethylene diamine/3-chloropropylalkoxysilane of at least 12/1, thereby forming a 3-[N-(2-aminoethyl)]aminopropylalkoxysilane. The reaction solution is fed back to the pot where the unreacted ethylene diamine in the reaction solution is evaporated again and then condensed for use in a next cycle of reaction. The apparatus includes a distillation pot, a reflux condenser, a feed means and a reactor connected to form a recirculating system.

10 Claims, 1 Drawing Sheet

METHOD AND APPARATUS FOR PREPARING 3-[N-(2-AMINOETHYL)]AMINOPROPYLALKOXYSILANE

BACKGROUND OF THE INVENTION

1. Field of the Invention

This invention relates to a method and apparatus for preparing 3-[N-(2-aminoethyl)]aminopropylalkoxysilanes useful as silane coupling agents or the like.

2. Prior Art

As is well known in the art, 3-[N-(2-aminoethyl)]aminopropylalkoxysilanes are widely used as silane coupling agents and effective for various modification purposes, for example, improving adhesion at the organic-inorganic interface, tailoring various resins and modifying surfaces.

For the synthesis of these compounds, one typical method is discloses in U.S. Pat. No. 2,971,864, Polish Patent No. 145,671, and J. Org. Chem., vol. 36, No. 21 (1971), 3120–3126, as reacting 3-chloropropylalkoxysilanes with ethylene diamine to form 3-[N-(2-aminoethyl)] aminopropylalkoxysilanes. This method is best known in the art. Stoichiometrically stated, this method uses 1 equivalent of 3-chloropropylalkoxysilane and 2 equivalents of ethylene diamine for synthesizing 1 equivalent of 3-[N-(2-aminoethyl)]aminopropylalkoxysilanes, with ethylene diamine hydrochloride being formed at the same time, as shown by the following reaction scheme.

$ClCH_2CH_2CH_2SiR^1{}_{3-n}(OR^2)_n + 2H_2NCH_2CH_2NH_2$

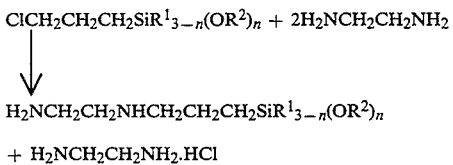

$H_2NCH_2CH_2NHCH_2CH_2CH_2SiR^1{}_{3-n}(OR^2)_n$ $+ H_2NCH_2CH_2NH_2 \cdot HCl$ In the formulae, each of $R^1$ and $R^2$ is an alkyl radical having 1 to 6 carbon atoms and n is equal to 1, 2 or 3.

In actual reaction, however, the end product 3-[N-(2-aminoethyl)]aminopropylalkoxysilanes further reacts with the starting reactants 3-chloropropylalkoxysilane and ethylene diamine to form bis-silyl products as shown below.

$ClCH_2CH_2CH_2SiR^1{}_{3-n}(OR^2)_n$ $+ H_2NCH_2CH_2NH_2$ $+ H_2NCH_2CH_2NHCH_2CH_2CH_2SiR^1{}_{3-n}(OR^2)_n$

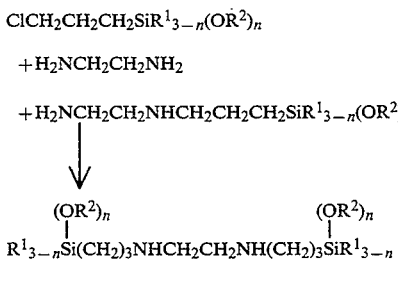

$R^1{}_{3-n}Si(CH_2)_3NHCH_2CH_2NH(CH_2)_3SiR^1{}_{3-n}$ with $(OR^2)_n$ groups $+ H_2NCH_2CH_2NH_2 \cdot HCl$ or $ClCH_2CH_2CH_2SiR^1{}_{3-n}(OR^2)_n$ $+ H_2NCH_2CH_2NH_2$ $+ H_2NCH_2CH_2NHCH_2CH_2CH_2SiR^1{}_{3-n}(OR^2)_n$

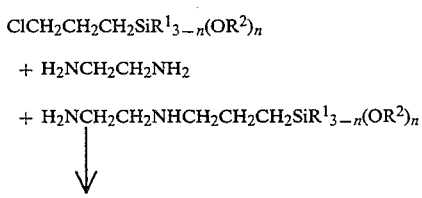

$H_2NCH_2CH_2N[CH_2CH_2CH_2SiR^1{}_{3-n}(OR^2)_n]_2$ $+ H_2NCH_2CH_2NH_2 \cdot HCl$ Various attempts were made to suppress side reactions since formation of these bis-silyl products remarkably lowers the yield of the end product 3-[N-(2-aminoethyl)]aminopropylalkoxysilane. For example, Japanese Patent Publication (JP-B) No. 1185/1965 discloses to react 4 to 6 equivalents of ethylene diamine with 1 equivalent of 3-chloropropylalkoxysilane. This method, however, is still insufficient in suppressing side reactions and low in the yield of the end product.

In JP-B 104891/1981, 7 to 10 equivalents of ethylene diamine is reacted with 1 equivalent of 3-chloropropylalkoxysilane. This method is effective for reducing formation of bis-silyl products and increasing the yield of the end product, but is a complex process since the excess ethylene diamine must be distilled out of the reaction system at the end of reaction. In addition, this method is low in production efficiency per batch since ethylene diamine is used in a large excess relative to 3-chloropropylalkoxysilane.

Also Japanese Patent Application Kokai (JP-A) Nos. 64031/1973 and 300192/1990 disclose a method for preparing 3-[N-(2aminoethyl)]aminopropylalkoxysilane by reacting hydroalkoxysilanes and N-allylethylene diamine in the presence of a platinum catalyst. This method, however, has the problem that the end product is of low purity because not only the end product 3-[N-(2-aminoethyl)]aminopropylalkoxysilane in gamma form is produced, but also beta form isomer, 2-[N-(2-aminoethyl)]amino-1-methylethylalkoxysilane is produced in large quantities. These isomers having approximate boiling points are difficult to separate.

Disclosed in JP-B 30313/1988 is a further method for preparing 3-[N-(2-aminoethyl)]aminopropylalkoxysilanes by reacting 2-cyanoethylalkoxysilanes with ethylene diamine and hydrogen gas in the presence of a heterogeneous catalyst of a metal selected from rhodium, platinum, and palladium. This method, however, requires to maintain high temperature and high pressure for a long period of time and is low in production efficiency per batch.

SUMMARY OF THE INVENTION

Therefore, an object of the present invention is to provide a novel and improved method and apparatus for preparing 3-[N-(2-aminoethyl)]aminopropylalkoxysilanes in high yields while suppressing formation of bis-silyl by-products as low as possible, which is characterized by a simple process, high volumetric yield and high production efficiency.

The present invention pertains to a method for preparing a 3-[N-(2-aminoethyl)]aminopropylalkoxysilane of the general formula (2):

$$H_2NCH_2CH_2NHCH_2CH_2CH_2SiR_{3-n}^1(OR^2)_n \qquad (2)$$

wherein $R^1$ and $R^2$ are independently an alkyl radical having 1 to 6 carbon atoms and n is equal to 1, 2 or 3 by reacting a 3- chloropropylalkoxysilane of the general formula (1):

$$ClCH_2CH_2CH_2SiR_{3-n}^1(OR^2)_n \qquad (1)$$

wherein $R^1$, $R^2$ and n are as defined above with ethylene diamine.

We have found the following procedure. First ethylene diamine is evaporated in a distillation pot heated to above the boiling point of ethylene diamine and then condensed in a reflux condenser. A 3-chloropropylalkoxysilane of formula (1) is supplied from its source to the condensed ethylene diamine in such a proportion that the molar ratio of ethylene diamine/3-chloropropylalkoxysilane is at least 12/1. The resulting mixture is maintained in a reactor for a sufficient time for reaction to proceed to completion. The reaction solution containing the end product, 3-[N-(2-aminoethyl)-]aminopropylalkoxysilane of formula (2) is fed back to the distillation pot where the unreacted ethylene diamine in the reaction solution is evaporated again. The ethylene diamine vapor is condensed in the condenser. Then the procedure is repeated by providing to the condensed ethylene diamine a new supply of 3-chloropropylalkoxysilane for reaction. By refluxing and recirculating ethylene diamine in this way, 3 to 5 equivalents of ethylene diamine can be eventually reacted with 1 equivalent of 3-chloropropylalkoxysilane.

Since this method ensures that reaction always takes place in a large excess of ethylene diamine and thus effectively restrains side reactions, the end product 3-[N-(2-aminoethyl)]aminopropylalkoxysilane can be produced in high yields. Since ethylene diamine is evaporated from the reaction solution after the completion of reaction, the end product is gradually concentrated in the distillation residue. Then the system eventually reaches the situation that 3 to 5 equivalents of ethylene diamine is reacted with 1 equivalent of 3-chloropropylalkoxysilane. This method is thus simple in process and has a high volumetric yield and high production efficiency. The present invention is predicated on this finding.

According to the present invention, there is provided a method for preparing a 3-[N-(2-aminoethyl)]aminopropylalkoxysilane by reacting a 3-chloropropylalkoxysilane of the general formula (1):

$$ClCH_2CH_2CH_2SiR^1{}_{3-n}(OR^2)_n \quad (1)$$

wherein $R^1$ and $R^2$ are independently an alkyl radical having 1 to 6 carbon atoms and n is equal to 1, 2 or 3, with ethylene diamine to produce a 3-[N-(2-aminoethyl)]aminopropylalkoxysilane of the general formula (2):

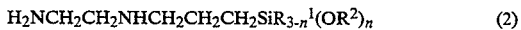

$$H_2NCH_2CH_2NHCH_2CH_2CH_2SiR^1{}_{3-n}(OR^2)_n \quad (2)$$

wherein $R^1$, $R^2$ and n are as defined as above The method includes the steps of: charging a distillation pot with ethylene diamine; heating the pot to at least the boiling point of ethylene diamine for evaporating ethylene diamine; condensing the ethylene diamine vapor into a liquid; mixing for reaction the liquid ethylene diamine with a 3-chloropropylalkoxysilane of formula (1) in such a proportion to give a molar ratio of ethylene diamine/3-chloropropylalkoxysilane of at least 12/1, thereby forming a 3-[N-(2-aminoethyl)]aminopropylalkoxysilane of formula (2); feeding the reaction solution back to the distillation pot; evaporating the unreacted ethylene diamine in the reaction solution again; and condensing the ethylene diamine vapor for use in a next cycle of reaction.

The present invention also provides an apparatus for preparing a 3-[N-(2-aminoethyl)]aminopropylalkoxysilane, comprising a distillation pot containing ethylene diamine therein which can be heated to at least the boiling point of ethylene diamine for evaporating ethylene diamine; a reflux condenser coupled to the pot for receiving and condensing the ethylene diamine vapor; feed means for feeding a 3-chloropropylalkoxysilane to the condensed ethylene diamine in a predetermined proportion; and a reactor coupled between the condenser and the pot for receiving a mixture of ethylene diamine and the 3-chloropropylalkoxysilane wherein reaction takes place for a predetermined time to form a 3-[N-(2-aminoethyl)]aminopropylalkoxysilane and having an exit for returning the reaction solution to the pot.

BRIEF DESCRIPTION OF THE DRAWINGS

The only figure, FIG. 1 schematically illustrates one exemplary apparatus according to the present invention.

DESCRIPTION OF THE PREFERRED EMBODIMENT

Figure 1:
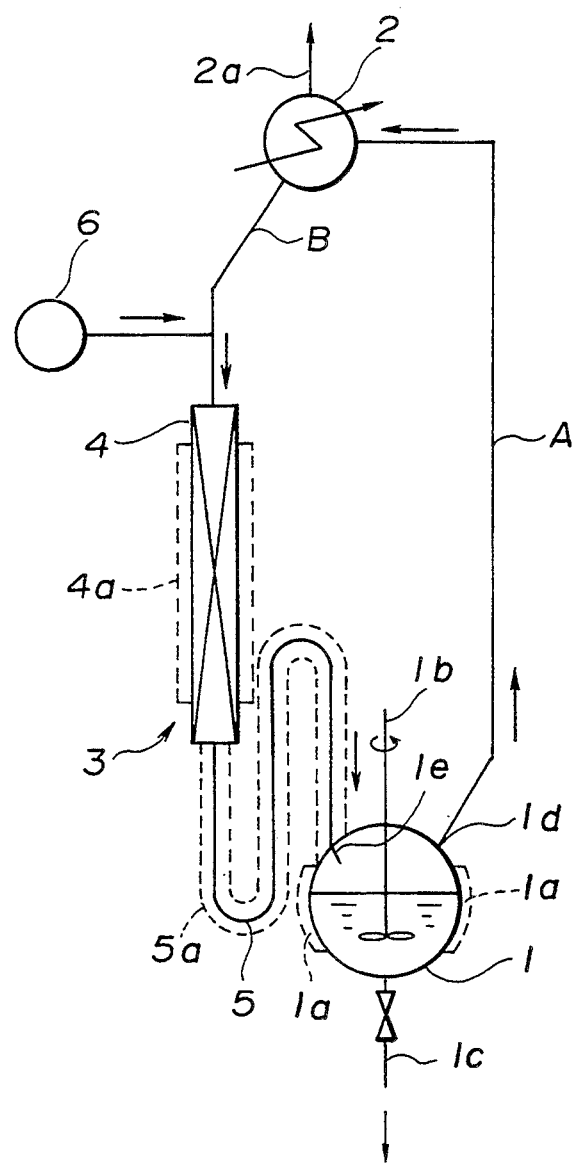

The present invention pertains to a method for preparing a 3-[N-(2-aminoethyl)]aminopropylalkoxysilane of formula (2) by reacting a 3-chloropropylalkoxysilane of formula (1) with a large excess of ethylene diamine while refluxing and recirculating ethylene diamine. The reaction scheme is shown below.

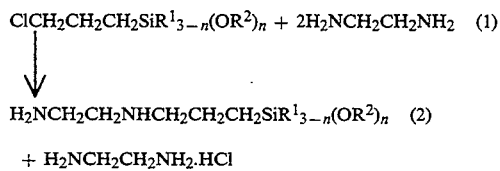

$$ClCH_2CH_2CH_2SiR^1{}_{3-n}(OR^2)_n + 2H_2NCH_2CH_2NH_2 \quad (1)$$
$$\downarrow$$
$$H_2NCH_2CH_2NHCH_2CH_2CH_2SiR^1{}_{3-n}(OR^2)_n \quad (2)$$
$$+ H_2NCH_2CH_2NH_2 \cdot HCl$$

In the formulae, $R^1$ and $R^2$ are independently an alkyl radical having 1 to 6 carbon atoms, for example, methyl, ethyl, propyl, butyl, pentyl and hexyl radicals, with the methyl and ethyl radicals being preferred. Letter n is equal to 1, 2 or 3.

Examples of the 3-chloropropylalkoxysilane of formula (1) include 3-chloropropyltrimethoxysilane, 3-chloropropylmethyldimethoxysilane, 3-chloropropyldimethylmethoxysilane, 3-chloropropyltriethoxysilane, 3-chloropropylmethyldiethoxysilane, 3-chloropropyldimethylethoxysilane, 3-chloropropylethyldimethoxysilane, 3-chloropropyldiethylmethoxysilane, 3-chloropropylethylmethylmethoxysilane, 3-chloropropylethyldiethoxysilane, 3-chloropropyldiethylethoxysilane, and 3-chloropropylethylmethylethoxysilane. These compounds are readily available and inexpensive.

Examples of the 3-[N-(2-aminoethyl)]aminopropylalkoxysilane of formula (2) include 3-[N-(2-aminoethyl)]aminopropyltrimethoxysilane, 3-[N-(2-aminoethyl)]aminopropylmethyldimethoxysilane, 3-[N-(2-aminoethyl)]aminopropyldimethylmethoxysilane, 3-[N-(2-aminoethyl)]aminopropyltriethoxysilane, 3-[N-(2-aminoethyl)]aminopropylmethyldiethoxysilane, 3-[N-(2-aminoethyl)]aminopropylethyldimethoxysilane, 3-[N-(2-aminoethyl)]aminopropyldiethylmethoxysilane, 3-[N-(2-aminoethyl)]aminopropylethylmethylmethoxysilane, 3-[N-(2-aminoethyl)]aminopropylethyldiethoxysilane, 3-[N-(2-aminoethyl)]aminopropyldiethylethoxysilane, and 3-[N-(2-aminoethyl)]aminopropylethylmethylethoxysilane.

The method of the invention is preferably practiced using an apparatus as described below. Referring to FIG. 1, there is illustrated one exemplary apparatus. The apparatus includes a distillation pot 1 containing ethylene diamine therein. The pot 1 is provided with a heater 1a for heating the pot or ethylene diamine at or above the boiling point of ethylene diamine a stirrer 1b for stirring the contents, a discharge port 1c at the bottom, and an outlet 1d for discharging evaporated ethylene diamine outside the pot. The pot 1 is also provided with an inlet 1e for receiving a reaction solution in which reaction of 3-chloropropylalkoxysilane with ethylene diamine has completed from a reactor as will be described later.

A reflux condenser 2 is connected to the pot vapor outlet 1d through a line A. The reflex condenser 2 is provided with a purging line 2a for purging air in the entire apparatus with nitrogen gas prior to the start of operation.

A reactor 3 includes a packed column 4 and a U-shaped reactor tube 5. The column 4 is filled with packings and has a top connected to the reflux condenser 2 through a line B and a bottom connected to an upstream end of the U-shaped tube 5. To line B is connected a supply 6 for feeding 3-chloropropylalkoxysilane. The U-shaped tube 5 has the upstream end and a downstream end which is connected to the pot 1 at the inlet 1e. The column 4 and tube 5 are covered with heaters 4a and 5a, respectively.

The apparatus is operated as follows. Ethylene diamine is evaporated in the pot 1 by means of the heater 1a and channeled through the outlet 1d and line A to the reflux condenser 2 where it is cooled and condensed into liquid. The ethylene diamine condensed in the condenser 2 is then mixed with 3-chloropropylalkoxysilane from the supply 6. The resulting mixture of ethylene diamine and 3-chloropropylalkoxysilane enters the packed column 4. Since the column 4 is packed with suitable packings and heated to a predetermined temperature by the heater 4a, the liquid mixture of ethylene diamine and 3-chloropropylalkoxysilane is quickly heated for reaction as it flows down the column. The reaction solution flowing down to the column bottom then enters the U-shaped reaction tube 4 which is also heated to a predetermined temperature by the heater 5a where the solution resides for a predetermined time until reaction is completed. The reaction solution in which reaction has completed is channeled from the reactor tube 5 to the distillation pot 1 again through the inlet 1e.

Since the distillation pot 1 must be heated at or above the boiling point (116.5° C.) of ethylene diamine, it is preferably heated at about 120° to 200° C., especially about 120° to 160° C. Ethylene diamine will not fully reflux at heating temperatures below 120° C. whereas the product coexisting in the pot can be colored or by-products having a higher boiling point can be formed at temperatures above 200° C.

The amount of 3-chloropropylalkoxysilane fed from the supply 6 to line B is adjusted relative to the flow rate of ethylene diamine condensed in the reflux condenser 2 such that the molar ratio of ethylene diamine/3-chloropropylalkoxysilane is at least 12, preferably from 12 to 20, especially from 13 to 17. The objects of the invention are not attained at a molar ratio of less than 12 because reaction proceeds incompletely so that more bis-silyl products are formed and the yield of the end product is reduced. A molar ratio in excess of 20 would rather detract from productivity because the effect associated with an increased amount of ethylene diamine would be negated and it would take a longer time to feed the necessary amount of 3-chloropropylalkoxysilane.

The liquid mixture containing a large excess of ethylene diamine relative to 3-chloropropylalkoxysilane undergoes reaction and reaches completion while it is heated in the packed column 4 and U-shaped tube 5. The heating temperature is preferably about 60° to 120° C., especially about 80° to 100° C. Reaction will proceed slowly at temperatures below 60° C. Above 120° C., ethylene diamine can boil within the reactor to prevent the reaction solution from flowing down the column.

It is to be noted that the packed column 4 is not limited in structure and any of distillation columns commonly used for distillation may be used. Its height may be determined from an economical aspect. The packing in the column 4 includes porcelain, glass, Raschig rings, bell saddles, and helix. Also useful are porous plates and wetted walls.

The U-shaped reaction tube 5 is of any desired dimensions as long as it can afford a sufficient residence or reaction time for reaction to proceed to completion.

Understandably, the reactor is not limited to the above-mentioned combination of a packed column and a serpentine tube and there may be used any desired type of reactor which allows a certain volume of reaction solution to reside therein and to be heated for driving reaction to completion. For example, a distillation pot as illustrated herein or a spiral tube both equipped with heating means may be used as the reactor.

In the practice of the invention, 3-chloropropylalkoxysilane reacts with ethylene diamine in the reactor 3 to form the end product 3-[N-(2-aminoethyl)]aminopropylalkoxysilane and ethylene diamine hydrochloride as shown below.

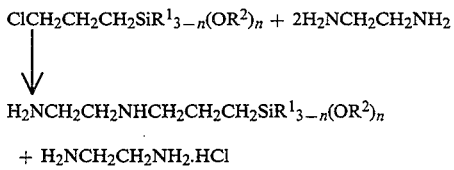

In the formulae, $R^1$, $R^2$ and n are as previously defined.

Since the molar ratio of ethylene diamine/3-chloropropylalkoxysilane is always kept at least 12 during reaction within the reactor, the end product is produced at an increased rate and formation of bis-silyl products which would decrease the yield of the end product is significantly restrained. At the end of reaction, the end product is present in admixture with ethylene diamine and forms a uniform liquid mixture because unreacted ethylene diamine which has not participate in reaction is in excess.

After the completion of reaction, the reaction solution is fed back to the distillation pot 1 where it is heated with stirring at or above the boiling point of ethylene diamine. At this stage, the end product 3-[N-(2-aminoethyl)]aminopropylalkoxysilane and ethylene diamine hydrochloride, which have higher boiling points, remain as a liquid mixture while the unreacted ethylene diamine which had not participated in reaction is evaporated again for recycle use.

As the recycle use of ethylene diamine is continued in this way, the end product and ethylene diamine hydrochloride are gradually concentrated in the distillation pot. Desirably the reaction is eventually terminated at a stage corresponding to the situation that about 3 to 5 equivalents of ethylene diamine has reacted with 1 equivalent of 3-chloropropylalkoxysilane. That is, further supply of 3-chloropropylalkoxysilane is stopped. Such a final reactant ratio is selected because the reaction solution in the pot becomes inhomogeneous and separates into an upper layer containing the end product and unreacted ethylene diamine and a lower layer containing ethylene diamine hydrochloride. Then the lower layer containing ethylene diamine hydrochloride is separated off. The layer containing the end product is distilled whereby the end product of higher purity is obtained in high yields.

If the amount of ethylene diamine reacted per equivalent of 3-chloropropylalkoxysilane is less than 3 equivalents, not only the upper layer containing the end product and the lower layer containing ethylene diamine hydrochloride would not definitely separate at the end of reaction, but also the amount of refluxing ethylene diamine would become short in the later stage of the process. The latter makes it difficult to maintain the molar ratio of ethylene diamine/3-chloropropylalkoxysilane at 12 or higher in the reactor, which obstructs the progress of reaction to completion and allows more bis-silyl products to form, resulting in a lower yield of the end product. Inversely, if the amount of ethylene diamine reacted per equivalent of 3-chloropropylalkoxysilane is more than 5 equivalents, the reaction solution in the pot would not separate into two distinct layers at the end of reaction. In order to enhance separation, an extra step of evaporating and distilling the excess, unreacted ethylene diamine out of the system is necessary at the end of process. This would make the entire process complex, resulting in a reduced volumetric efficiency and low productivity.

The above-mentioned reaction is preferably carried out between ethylene diamine and 3-chloropropylalkoxysilane only, that is, in the absence of a solvent. Although reaction can be effected in a solvent which is inert to the reactants and reaction products, such a solvent has no particular favorable effect on reaction and would rather hinder the separation of the ethylene diamine hydrochloride layer, resulting in a lowing of production efficiency.

It is also preferred to perform reaction in the absence of water and in an atmosphere of an inert gas which is inert to the reactants and reaction products, for example, nitrogen and argon. If water is present in the reaction system, the reactant 3-chloropropylalkoxysilane and the product 3-[N-(2-aminoethyl)]aminopropylalkoxysilane could condense through hydrolysis, with methanol being by-produced which can lower the system temperature by depriving heat of evaporation, inhibiting ethylene diamine from refluxing.

Preferably reaction is performed under atmospheric pressure or about 760 mmHg although reduced pressures of about 10 mmHg to increased pressures are acceptable. Above atmospheric pressure, the temperature of the distillation pot must be further raised.

EXAMPLE

Examples of the invention are given below by way of illustration and not by way of limitation.

Example 1

Using the apparatus shows in FIG. 1, 3-[N-(2-aminoethyl)]aminopropyltrimethoxysilane was prepared.

In the apparatus, the packed column 4 was a column made of Pyrex ® glass having an inner diameter of 20 mm and a length of 700 mm packed with glass rings. The U-shaped tube 5 having the upstream end connected to the packed column bottom was a serpentine tube of Teflon ® having an inner diameter of 10 mm and an entire length of 1,300 mm, which extended vertically downward 300 mm from the packed column bottom, turned upward thereat, extended vertically upward 130 mm above the packed column bottom, turned downward thereat again, and extended vertically downward to the connection to the inlet 1e of the distillation pot 1. The distillation pot 1 was of glass and had an interior volume of 5,000 ml.

The system was fully purged of air by feeding nitrogen from the purge line 2a. The distillation pot 1 was charged with 2,506 g (41.7 mol) of ethylene diamine, the stirrer. 1b was operated, and the heater 1a was actuated to heat the ethylene diamine at 120° C. for boiling. The ethylene diamine passed in vapor form from the pot 1 to the reflux condenser 2 through the vapor outlet 1d and line A, condensed into liquid in the condenser 2, entered and flowed down the packed column 4, passed through the U-shaped tube 5 over a sufficient residence time, and returned to the distillation pot 1. The packed column 4 and U-shaped tube 5 were maintained at 85° to 95° C. by means of the heaters 4a and 5a, respectively. The ethylene diamine condensed in the condenser 2 flowed down the packed column 4 at a flow rate of 29.25 g/min. (0.487 mol/min.)

Then 2205 g (11.1 mol) of 3-chloropropyltrimethoxysilane, which corresponded to a final equivalent ratio of ethylene diamine/3-chloropropyltrimethoxysilane of 3.76, was fed from the supply 6 at a flow rate of 5.73 g/min. (0.029 mol/min.) whereupon ethylene diamine and 3-chloropropyltrimethoxysilane were reacted through the packed column 4 and U-shaped tube 5. At this point, the molar ratio of ethylene diamine/3-chloropropyltrimethoxysilane was 16.9. The entire amount of 3-chloropropyltrimethoxysilane was fed over 6.4 hours. The system was operated for ripening for a further 1 hour while keeping ethylene diamine refluxing. During the process, the distillation pot 1 was heated to maintain the reflux state of ethylene diamine and the above-specified amount of ethylene diamine condensed. The temperature within the pot 1 raised from 120° C. to 145° C.

At the end of the process, 3-[N-(2-aminoethyl)-]aminopropyltrimethoxysilane and ethylene diamine hydrochloride resulting from the reaction accumulated in the pot 1 to a volume of about 4,700 ml. The reaction solution was cooled to 40° to 50° C. whereupon it separated into two layers. The lower layer of ethylene diamine hydrochloride (1899 g) was separated off through the bottom discharge port 1c. Next, the upper layer containing the end product, 2805 g, was purified by simple distillation. There was isolated 2237 g of 3-[N-(2-aminoethyl)]aminopropyltrimethoxysilane. The yield was 91% calculated on the basis of 3-chloropropyltrimethoxysilane. On gas chromatography analysis, the end product 3-[N-(2-aminoethyl)]aminopropyltrimethoxysilane was 99.4% pure.

Example 2

Using the apparatus shown in FIG. 1, 3-[N-(2-aminoethyl)]aminopropylmethyldimethoxysilane was prepared.

In the apparatus, the packed column 4 was a column made of Pyrex ® glass having an inner diameter of 20 mm and a length of 700 mm packed with glass rings. The U-shaped tube 5 having the upstream end connected to the packed column bottom was a serpentine tube of Teflon ® having an inner diameter of 10 mm and an entire length of 3,000 mm, which extended vertically downward 1,050 mm from the packed column bottom, turned upward thereat, extended vertically upward 130 mm above the packed column bottom, turned downward thereat again, and extended vertically. downward to the connection to the inlet 1e of the distillation pot 1. The distillation pot 1 was of glass and had an interior volume of 5,000 ml.

The system was fully purged of air by feeding nitrogen from the purge line 2a. The distillation pot 1 was charged with 2,506 g (41.7 mol) of ethylene diamine, the stirrer 1b was operated, and the heater 1a was actuated to heat the ethylene diamine at 120° C. for boiling. The ethylene diamine passed in vapor form from the pot 1 to the reflux condenser 2 through the vapor outlet 1d and line A, condensed into liquid in the condenser 2, entered and flowed down the packed column 4, passed through the U-shaped tube 5 over a sufficient residence time, and returned to the distillation pot 1. The packed column 4 and U-shaped tube 5 were maintained at 85° to 95° C. by means of the heaters 4a and 5a, respectively. The ethylene diamine condensed in the condenser 2 flowed down the packed column 4 at a flow rate of 41.03 g/min. (0.683 mol/min.)

Then 2028 g (11.1 mol) of 3-chloropropylmethyldimethoxysilane, which corresponded to a final equivalent ratio of ethylene diamine/3-chloropropylmethyldimethoxysilane of 3.76, was fed from the supply 6 at a flow rate of 7.48 g/min. (0.041 mol/min.) whereupon ethylene diamine and 3-chloropropylmethyldimethoxysilane were reacted through the packed column 4 and U-shaped tube 5. At this point, the molar ratio of ethylene diamine/3-chloropropylmethyldimethoxysilane was 16.7. The entire amount of 3-chloropropylmethyldimethoxysilane was fed over 4.5 hours. The system was operated for ripening for a further 1 hour while keeping ethylene diamine refluxing. During the process, the distillation pot 1 was heated to maintain the reflux state of ethylene diamine and the above-specified amount of ethylene diamine condensed. The temperature within the pot 1 raised from 120° C. to 150° C.

At the end of the process, 3-[N-(2-aminoethyl)-]aminopropylmethyldimethoxysilane and ethylene diamine hydrochloride resulting from the reaction accumulated in the pot 1 to a volume of about 4,500 ml. The reaction solution was cooled to 40° to 50° C. whereupon it separated into two layers. The lower layer of ethylene diamine hydrochloride (1847 g) was separated off through the bottom discharge port 1c. Next, the upper layer containing the end product, 2636 g, was purified by simple distillation. There was isolated 2092 g of 3-[N-(2-aminoethyl)]aminopropylmethyldimethoxysilane. The yield was 91% calculated on the basis of 3-chloropropylmethyldimethoxysilane. On gas chromatography analysis, the end product 3-[N-(2-aminoethyl)-]aminopropylmethyldimethoxysilane was 99.3% pure.

Example 3

The process of Example 1 was repeated in the same apparatus except that 3-chloropropyltrimethoxysilane was fed at a flow rate of 7.62 g/min. (0.038 mol/min. ) which provided a molar ratio of 12.7. The yield of 3-[N-(2-aminoethyl)]aminopropyltrimethoxysilane was 88% calculated on the basis of 3-chloropropyltrimethoxysilane.

Comparative Example 1

The process of Example 1 was repeated in the same apparatus except that 3-chloropropyltrimethoxysilane was fed at a flow rate of 9.49 g/min. (0.048 mol/min.) which provided a molar ratio of 10.2. The yield of 3-[N-(2-aminoethyl)]aminopropyltrimethoxysilane was 76% calculated on the basis of 3-chloropropyltrimethoxysilane. The amount of bis-silyl products formed increased and the yield of the end product lowered.

Comparative Example 2

In this example, 3-[N-(2-aminoethyl)]aminopropyltrimethoxysilane was prepared by a conventional method.

A 200-ml, four necked glass flask equipped with a stirrer, reflux condenser, and thermometer was charged with 72.0 g (1.2 mol) of ethylene diamine and heated at 112° to 117° C. From a dropping funnel, 59.6 g (0.3 mol) of 3-chloropropyltrimethoxysilane was added dropwise to the flask over 2 hours (the molar ratio of ethylene diamine/3-chloropropyltrimethoxysilane=4.0). After one hour ripening, the reaction solution was transferred to a separatory funnel and cooled for allowing the solution to separate into two layers. The lower layer of ethylene diamine hydrochloride was separated off. The upper layer containing 3-[N-(2-aminoethyl)]aminopropyltrimethoxysilane was taken out and purified by simple distillation, obtaining 46.8 g of 3-[N-(2-aminoethyl)]aminopropyltrimethoxysilane. The yield was 70.1%. A substantial amount of bis-silyl products was detected.

Comparative Example 3

The conventional method was carried out while using an excess of ethylene diamine relative to 3-chloropropyltrimethoxysilane.

A 300-ml, four necked glass flask equipped with a stirrer, reflux condenser, and thermometer was charged with 180.0 g (3.0 mol) of ethylene diamine and heated at 80° to 90° C. From a dropping funnel, 74.4 g (0.37 mol) of 3-chloropropyltrimethoxysilane was added dropwise to the flask over 1.25 hours (the molar ratio of ethylene diamine/3-chloropropyltrimethoxysilane=8.11). After one hour ripening, the reaction solution was heated until boiling whereupon 82.3 g (1.37 mol) of ethylene diamine was distilled out of the system through a reflux outlet port. The concentrated reaction solution was transferred to a separatory funnel and cooled for allowing the solution to separate into two layers. The lower layer of ethylene diamine hydrochloride was separated off. The upper layer containing 3-[N-(2-aminoethyl)-]aminopropyltrimethoxysilane was taken out and purified by simple distillation, obtaining 67.2 g of 3-[N-(2-aminoethyl)]aminopropyltrimethoxysilane. The yield was 81.7%.

In this example, formation of bis-silyl products was not fully suppressed. Since ethylene diamine was used in a large excess relative to 3-chloropropyltrimethoxysilane, both production efficiency and volumetric efficiency were low.

The method and apparatus of the invention are effective for producing 3-[N-(2-aminoethyl)]aminopropylalkoxysilanes through a simple process in high yields, at high volumetric efficiency, and at high production efficiency while minimizing formation of by-products.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing a 3-[N-(2-aminoethyl)aminopropylalkoxysilane of formula (2):

$$H_2NCH_2CH_2NHCH_2CH_2CH_2SiR_{3-n}^1(OR^2)_n \qquad (2)$$

wherein $R^1$ and $R^2$ are each independently $C_{1-6}$-alkyl, and n is 1, 2, or 3, comprising:
reacting a 3-chloropropylalkoxysilane of formula (1):

$$ClCH_2CH_2CH_2SiR_{3-n}^1(OR^2)_n \qquad (1)$$

wherein $R^1$, $R^2$ and n are as defined above with ethylene diamine, comprising:
charging a distillation pot with ethylene diamine,
heating the pot to at least the boiling point of ethylene diamine to evaporate ethylene diamine,
condensing the ethylene diamine vapor into a liquid in a reflux condenser,
mixing the liquid ethylene diamine with a 3-chloropropylalkoxysilane of formula (1) in a molar ratio of ethylene diamine/3-chloropropylalkoxysilane of at least 12/1,
reacting the mixture of ethylene diamine and 3-chloropropylalkoxysilane in a reactor, thereby forming a 3-[N-(2-aminoethyl)]aminopropylalkoxysilane of formula (2)
feeding a reaction solution containing ethylene diamine and 3-[N-(2-aminoethyl)]aminopropylalkoxysilane from the reactor back to the distillation pot and repeating the method by again evaporating the unreacted ethylene diamine in the reaction solution, and
condensing the ethylene diamine vapor for use in a next cycle of reaction.

2. The method of claim 1 wherein 3 to 5 equivalents of ethylene diamine is eventually reacted per equivalent of the 3-chloropropylalkoxsilane of formula (1).

3. In a method for the preparation of 3-[N-(2-aminoethyl)]aminopropylalkoxysilane of formula (2)

$$H_2NCH_2CH_2NHCH_2CH_2CH_2SiR_{3-n}^1(OR^2)_n \qquad (2)$$

wherein $R^1$ and $R^2$ are each independently $C_{1-6}$-alkyl, and n is 1–3, comprising:
reacting a 3-chloropropylalkoxysilane of formula (1):

$$ClCH_2CH_2CH_2SiR_{3-n}^1(OR^2)_n \qquad (1)$$

with a molar excess of ethylene diamine, the improvement wherein a mixture of a product of formula (2) and unreacted ethylene diamine are distilled so as to evaporate ethylene diamine, said ethylene diamine being condensed and returned to the reaction with 3-chloropropylalkoxysilane such that the molar ratio of ethylene diamine/3-chloropropylalkoxysilane is at least 12/1.

4. A method according to claim 3 wherein during the course of the reaction, 3 to 5 equivalents of ethylene diamine react with each equivalent of 3-chloropropylalkoxysilane overall.

5. A method according to claim 3, wherein the reaction is performed in the absence of water and in an inert gas atmosphere.

6. A method according to claim 3, wherein the reaction is performed under atmospheric pressure.

7. A method according to claim 3, wherein $R^1$ and $R^2$ are each independently methyl or ethyl.

8. A method according to claim 3, wherein the compound of formula (1) is:
3-chloropropyltrimethoxysilane,
3-chloropropylmethyldimethoxysilane,
3-chloropropyldimethylmethoxysilane,
3-chloropropyltriethoxysilane,
3-chloropropylmethyldiethoxysilane,
3-chloropropyldimethylethoxysilane,
3-chloropropylethyldimethoxysilane,
3-chloropropyldiethylmethoxysilane,
3-chloropropylethylmethylmethoxysilane,
3-chloropropylethyldiethoxysilane,
3-chloropropyldiethylethoxysilane, or
3-chloropropylethylmethylethoxysilane.

9. A method according to claim 2, wherein the compound of formula (2) is:
3-[N-(2-aminoethyl)]aminopropyltrimethoxysilane,
3-[N-2-aminoethyl)]aminopropylmethyldimethoxysilane,
3-[N-(2-aminoethyl)]aminopropyldimethylmethoxysilane,
3-[N-(2-aminoethyl)]aminopropyltriethoxysilane,
3-[N-(2-aminoethyl)]aminopropylmethyldiethoxysilane,
3-[N-(2-aminoethyl)]aminopropylethyldimethoxysilane,
3-[N-(2-aminoethyl)]aminopropyldiethylmethoxysilane,
3-[N-(2-aminoethyl)aminopropylethylmethylmethoxysilane,
3-[N-(2-aminoethyl)[aminopropylethyldiethoxysilane,
3-[N-(2-aminoethyl)]aminopropyldiethylethoxysilane, or
3-[N-(2-aminoethyl)]aminopropylethylmethylethoxysilane.

10. An apparatus for preparing 3-[N-(2-aminoethyl)]aminopropylalkoxysilane, comprising:
a distillation pot containing ethylene diamine therein which can be heated to at least the boiling point of ethylene diamine for evaporating ethylene diamine,
a refulx condenser coupled to the pot for receiving and condensing the ethylene diamine vapor,
feed means for feeding a 3-chloropropylalkoxysilane to the condensed ethylene diamine in a predetermined proportion, and
a reactor comprising a packed column having a bottom and a U-shaped reactor tube having one end connected to the column bottom, said packed column being connected to the reflux condenser and said tube being connected to the pot, the reactor receiving a mixture of ethylene diamine and the 3-chloropropylalkoxysilane wherein reaction takes place for a predetermined time to form a 3-[N-(2-aminoethyl)]aminopropylalkoxysilane,
said U-shaped reactor tube having such a dimension that it affords a sufficient residence or reaction time for reaction to proceed to completion in order to feed the reaction solution containing ethylene diamine and 3-[N-(2-aminoethyl)]aminopropylalkoxysilane back to the distillation pot.

* * * * *